United States Patent
Ledford, Jr.

(10) Patent No.: US 7,258,726 B2
(45) Date of Patent: Aug. 21, 2007

(54) METHOD AND APPARATUS FOR MEASURING VELOCITY OF CHROMATOGRAPHIC PULSE

(75) Inventor: Edward B. Ledford, Jr., Lincoln, NE (US)

(73) Assignee: Zoex Licensing Corporation, Houston, TX (US)

( * ) Notice: Subject to any disclaimer, the term of this patent is extended or adjusted under 35 U.S.C. 154(b) by 313 days.

(21) Appl. No.: 10/508,647

(22) PCT Filed: Mar. 19, 2002

(86) PCT No.: PCT/US02/08488

§ 371 (c)(1), (2), (4) Date: Sep. 17, 2004

(87) PCT Pub. No.: WO03/082427

PCT Pub. Date: Oct. 9, 2003

(65) Prior Publication Data

US 2005/0139076 A1    Jun. 30, 2005

(51) Int. Cl.
*B01D 53/02* (2006.01)

(52) U.S. Cl. ........ 95/82; 95/87; 96/101; 73/23.35; 73/23.39

(58) Field of Classification Search ........ 96/101, 96/102, 105; 95/82, 87; 73/23.35, 23.39, 73/23.41, 23.42; 422/89

See application file for complete search history.

(56) References Cited

U.S. PATENT DOCUMENTS

| | | | |
|---|---|---|---|
| 3,305,000 A | 2/1967 | Bullen et al. | |
| 3,309,504 A | 3/1967 | Rosso et al. | |
| 4,948,389 A * | 8/1990 | Klein et al. | 95/87 |
| 5,215,556 A | 6/1993 | Hiller et al. | |
| 5,596,876 A | 1/1997 | Manura et al. | |
| 6,190,613 B1 * | 2/2001 | Watanabe et al. | 422/89 |
| 2001/0037727 A1 | 11/2001 | Ledford, Jr. et al. | |

* cited by examiner

*Primary Examiner*—Duane Smith
*Assistant Examiner*—Robert Clemente
(74) *Attorney, Agent, or Firm*—Kilyk & Bowersox, P.L.L.C.

(57) ABSTRACT

An Apparatus and method for two-stage chromatographic separation uses thermal modulation. The chromatographic column or modulation tube (1) has a loop structure such that two portions of modulation tube (1) can be thermally modulated simultaneously by at least one thermal modulation device, which device can have a cold gas source, jet tube (2), and a hot gas source, hot jet tube (5), to modulate the temperature of the portions (3, 4) of modulation tube (1).

23 Claims, 6 Drawing Sheets

SIDE VIEW

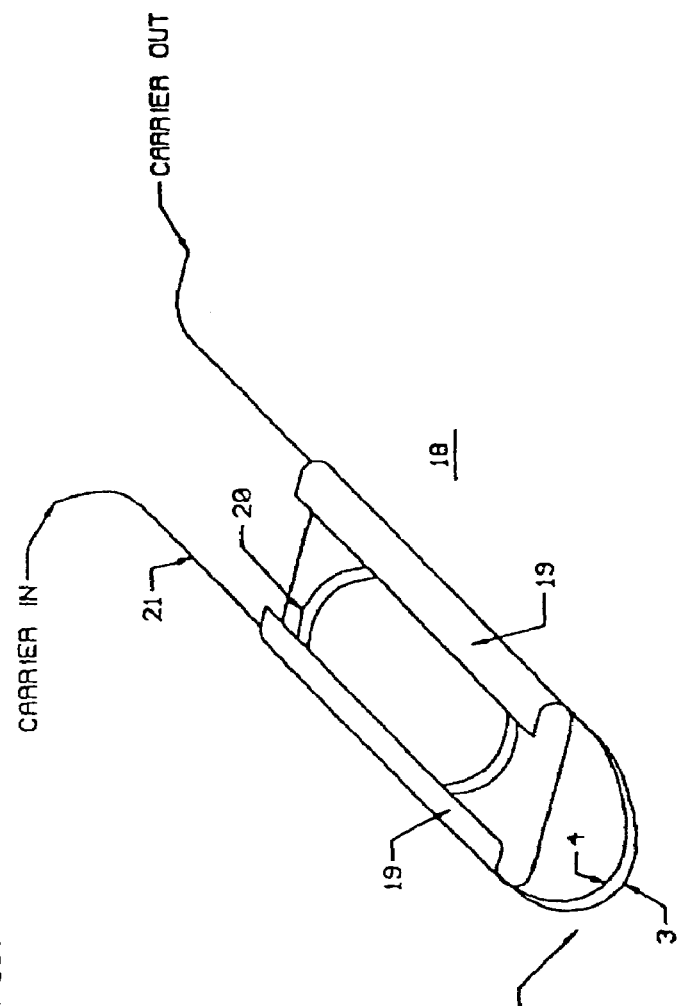
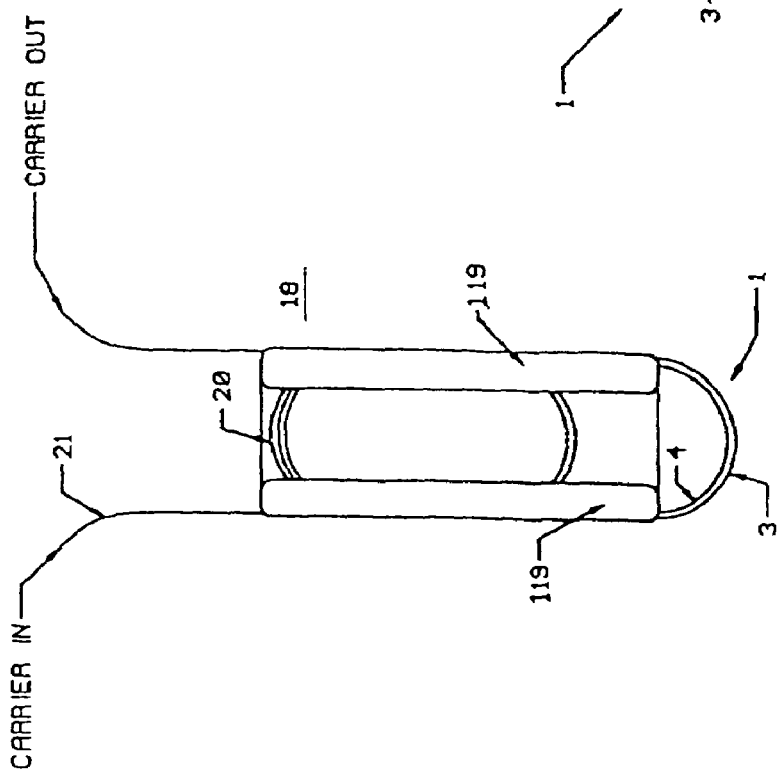

METHOD AND APPARATUS FOR MEASURING VELOCITY OF CHROMATOGRAPHIC PULSE

FIELD OF THE INVENTION

This invention relates to the field of gas chromatography.

BACKGROUND OF THE INVENTION

Prior Art Thermal Modulation

Thermal modulation is a means of producing chemical pulses of short duration in capillary gas chromatographic columns.

Thermal modulators grew out of prior art ohmically heated cryogenic traps, which received attention in the scientific literature for some years, following demonstration by Hopkins and Pretorious that ohmic heating of cryogenic traps was faster than the heating obtained with a hot gas stream. (B. J. Hopkins, and V. Pretorious, Journal of Chromatography, 158 (1978) 471). A number of ohmically heated single stage thermal modulators were reported, examples of which are described in the following publications, incorporated in their entireties herein by reference:

1. J. Phillips, et al. "Thermal Desorption Modulation as a Replacement for Sample Injection in Very-Small-Diameter Gas Chromatography Capillary Columns", Journal of Chromatographic Science 1986, vol. 24, pp. 396-399.)
2. S. Springston. "Cryogenic-focussing, ohmically heated on-column trap for capillary gas chromatography." Journal of Chromatography, 517 (1990) 67-75.
3. A. van Es, J. Janssen, C. Cramers, and J. Rijks. "Sample Enrichment in High Speed Narrow Bore Capillary Gas Chromatography", Journal of High Resolution Chromatography and Chromatography Communications, 11 (1988) 852-857.

Single stage modulators, such as those described in the above publications, were found to concentrate and release sample substances as sharp chemical pulses, but suffered certain limitations. First, ohmic films having very low thermal inertia had to be overdriven in order to heat underlying capillary column segments having much higher thermal inertias. Overdriving caused ohmic coatings to burn out at unpredictable times. A further limitation of the above designs was undesirable tailing of the concentration pulses generated, which limited the utility of the devices for sampling continuous, or semi-continuous sample streams, such as the effluent of an analytical GC column.

The tailing observed with single stage thermal modulators was eliminated by the two-stage thermal modulator introduced by Phillips and Liu, as described in U.S. Pat. Nos. 5,135,549 and 5,196,039, and European Patent No. 0522150, which are incorporated in their entireties herein. Two-stage thermal modulators produced sharp and symmetrical chemical pulses by refocusing a chemical pulse emitted from a first modulator stage at the head of a second thermal modulator stage downstream of the first. The two modulator stages are pulse-heated and cooled 180° out of phase with one another, in order to achieve the refocusing effect. The device proved its ability to sample semi-continuous sample streams in a capillary tube, such as the effluent from an analytical column. This functionality gave rise to the startling advance of comprehensive two-dimensional gas chromatography. As originally implemented, however, ohmically heated two-stage thermal modulators burned out frequently, and unpredictably, and were moreover difficult to prepare and handle.

Ledford and Phillips introduced a solution to the burnout problem, as described in U.S. Pat. No. 6,007,602, which is incorporated in it entirety herein. Although their heater system was reliable, their implementation employed moving parts in the vicinity of the column, which made the device difficult to manufacture and handle in the field. A moving cooler system attributable to Marriott (see for example R. M. Kinghorn and P. J. Marriott, "Enhancement of Signal-to-Noise Ratios in Capillary Gas Chromatography by Using A Longitudinally Modulated Cryogenic System", Journal of High Resolution Chromatography, 21 (1998) 32-38) suffered similar disadvantages.

Ledford et al eliminated problems associated with moving parts in the vicinity of the column by introducing a two-stage thermal modulator employing pulsed heated and cooled gas jets, described in U.S. Provisional Patent Application No. 60/175,727, filed Jan. 12, 2000, and PCT application WO 01/51170 PCT/US01/01065, filed Jan. 12, 2001, which are incorporated in their entireties herein by reference. The jet modulator was relatively easy to manufacture and use, and produced excellent thermal modulations, including the surprising ability to modulate volatile substances, such as methane. The principle drawback of this design was the complexity of the apparatus, which employed four valves, a heat exchanger, and a bulky mechanical assembly for positioning a modulator tube in the paths of pulsed hot and cold jets.

A variation of the jet modulator was introduced by Beens (J. Beens, et al. "Simple, non-moving modulation interface for comprehensive two-dimensional gas chromatography" *Journal of Chromatography A,* 919 (1) (2001) pp. 127-132, which is incorporated in its entirety herein by reference.) Beens employed two high pressure valves to pulse jets of liquid carbon dioxide onto two portions of a capillary tube in the manner known to effect two-stage thermal modulation. The jets were separated by about ten centimeters within the GC oven. Unlike the device of Ledford et al, Beens did not employ gas jets to heat the cooled stages of the modulator tube, but rather relied on the stirred oven bath of the gas chromatograph to heat the modulator stages. To this end, Beens positioned the column on a sprung metal bracket carrying conventional column fittings. This bracket tensioned the modulator tube, held it in the paths of the $CO_2$ jets, and was an open structure that exposed the modulator tube to the oven bath. When applied to comprehensive two-dimensional gas chromatography, Beens's system generated high quality GC×GC images.

Even with the admirable simplicity and good performance of the Beens design, certain limitations were encountered. First, liquid carbon dioxide refrigerant employed in the cold jets produces jet gas temperatures of about −77° C., unsuitable for modulation of chemical compounds with volatilities greater than that of octane. This is problematical for important samples such as gasoline and naptha, in which modulation over the C5+ range, or lower carbon numbers, is desirable. Second, the carbon dioxide consumption rate of the jets was high enough (c.a. 200 std. liters/min, semi-continuous) to pose safety risks in the event of ventilation failure in the room. Third, dead volume between the valves and the jet nozzles could be cleared rapidly only at high gas flow rates. At low gas flow rates, it would be questionable whether the dead volumes would clear rapidly enough to permit high quality thermal modulation. Thus the Beens device requires fairly high gas flow rates through the cold jets. Fourth, high pressure valves present risks to operators that low-pressure valves do not, and are moreover expensive. Fifth, carbon dioxide was admitted to the modulator tube by means of precision fabricated nozzles, which were artful to construct. Sixth, the observed chemical pulse width generated by the Beens device was on the order of 60 to 70 milliseconds, as compared to 36 milliseconds with systems employing hot jet heating of the modulator stages. Narrow pulse widths are desirable in thermal modulation, because well-focused chemical pulses translate to improved sensitivity and resolution in gas chromatographic instruments. Seventh, permanent frost spots appeared on the capillary columns when the cold jets were pulsed at high frequencies, indicating that the heating rate provided by an ambient oven limits the frequency at which the modulator could operate. High frequency modulation is desirable in some applications, such as sensitivity enhancement of one-dimensional gas chromatography, or high speed GC×GC. Eighth, threading columns through a pair of fittings doubled the work of installing columns into the GC oven.

Various embodiments of the prior art are taught, for example, in U.S. Pat. No. 5,135,549 to Phillips et al., printed on Aug. 4, 1992, U.S. Pat. No. 5,196,039 to Phillips et al., printed on Mar. 23, 1993, U.S. Pat. No. 6,007,602 to Ledford et al., printed on Dec. 28, 1999, and U.S. patent application Ser. No. 09/760,508 to Ledford et al., filed on Jan. 12, 2001, which are hereby incorporated in their entireties by reference.

In view of various limitations of prior art thermal modulators, this inventor believed that further innovation in jet modulator technology was needed.

SUMMARY OF THE PRESENT INVENTION

The present invention is the result of several discoveries concerning the nature and operation of jet modulators. This inventor has found:

Low-flow cold jets (10 std. liter per minute gas flow rate) are capable of cooling a modulator stage located 3 millimeters away from the jet outlet, even when the modulator stage is exposed to the stirred oven bath of a gas chromatograph. This discovery simplified mounting modulator tubes in the path of jets, which can now be done with a cartridge structure having no column fittings.

Jet modulators work significantly better with pulsed hot jets than without.

A high-flow hot jet can divert a low-flow cold jet away from the modulator tube, thereby permitting the cold jet to be operated continuously, rather than pulsed with a valve. This discovery led to simplification of apparatus.

By looping a modulator tube more than once through the path of a cold jet, and heating the multiplicity of cold spots thus formed with a single pulsed hot jet, multi-stage thermal modulation is achieved with apparatus comprising a single low cost valve operated at low pressure. This discovery further simplified apparatus.

The so-called "loop modulator" permits in-situ measurement of the velocity of a chemical substance within the body of a capillary tube, as well as detailed characterization of the thermal modulation process. These unanticipated benefits are particularly welcome: they permit new methods for the study of physical and physico-chemical processes in capillary tubes.

It is an object of the present invention to provide a novel method for multi-stage thermal modulation.

It is an object of the present invention to provide a novel apparatus for multi-stage thermal modulation.

It is an object of the present invention to implement multi-stage thermal modulation with a single pulsed valve.

It is an object of the present invention to provide a novel means of measuring the velocity of a chemical substance traveling through a capillary tube.

It is an object of the present invention to provide a capillary column holder that is robust in its construction, and easy to use.

It is an object of the present invention to provide a multi-stage thermal modulator suitable for comprehensive two-dimensional gas chromatography (GC×GC).

It is an object of the present invention to provide a means for multi-stage thermal modulation that is sufficiently inexpensive, manufacturable, and easy to use, as to be a commercially viable product in the field of gas chromatography.

In accordance with these and other purposes of the invention, a method of thermal modulation is provided whereby a single pulsed valve effects high quality multi-stage thermal modulation, and permits the velocity of a chemical substance in a capillary tube sustaining a flow of carrier gas to be measured.

Furthermore, apparatus is provided, comprising a retention alteration means, gas jet means, a modulator tube, and means for manipulating the temperature of a modulator tube, said apparatus providing thermal modulation of chemical substances admixed with a carrier gas and flowing through a tube.

BRIEF DESCRIPTION OF THE DRAWINGS

The present invention will be better understood with reference to the accompanying drawings, which describe a "loop modulator" embodiment satisfying the objects of invention.

FIG. 1a is a side view of an embodiment of the present invention showing a cold gas jet tube, a hot gas jet tube, and a loop modulator;

FIG. 1b is a front view of the embodiment shown in FIG. 1a;

FIG. 2 depicts a detailed cross-sectional side view of the embodiment shown in FIG. 1a;

FIG. 3a is a top view of an embodiment of the present invention showing a first and a second modulator stage;

FIG. 3b is a perspective view of the embodiment shown in FIG. 3a;

Figure 1:
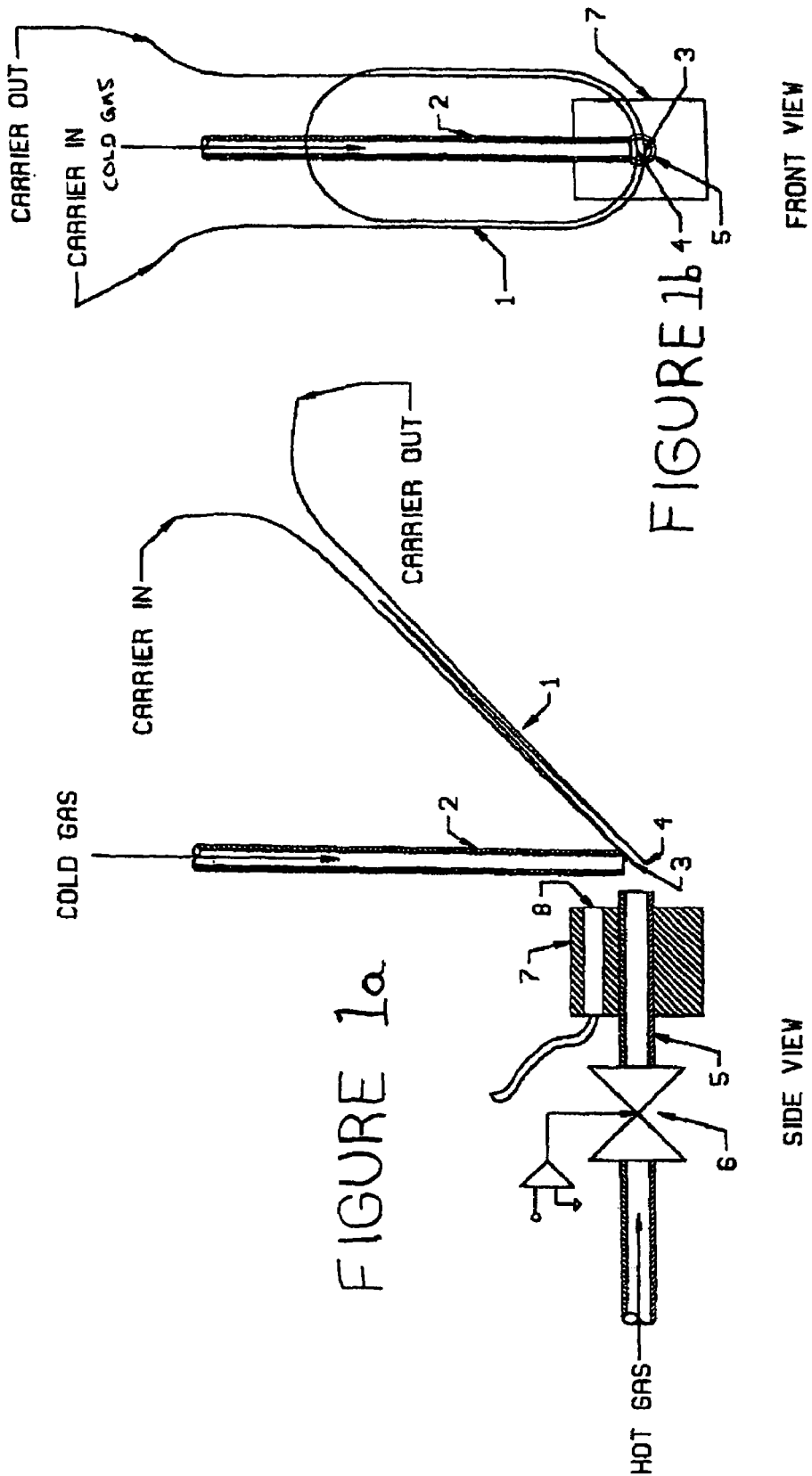

Other various embodiments of the present invention will be apparent to those skilled in the art in consideration of the specification and practice of the invention described herein, and the detailed description that follows. It is intended that the specification and examples be considered as exemplary only, and that the true scope and spirit of the invention includes those other various embodiments.

DETAILED DESCRIPTION OF THE INVENTION

The present invention can be further described in terms of the following methods and apparatus:

A method, herein referred to as method "A," comprises a method of thermal modulation for generating chemical pulses in a fluid stream flowing through a modulator tube, said method comprising the steps of:
  a. providing a modulator tube comprising an inlet, a first portion in communication with said inlet, a second portion in communication with said first portion, and an outlet portion in communication with said second portion;
  b. creating a fluid stream in a direction through the modulator tube to produce a carrier fluid stream;
  c. introducing a sample into the carrier fluid stream, said sample comprising one or more chemical substances;
  d. manipulating the temperature of the first portion to cause at least a portion of the sample to be retained therein;
  e. manipulating the temperature of the second portion such that at least a portion of the sample will be retained therein;
  f. accumulating a sample component in the first portion for a period of time to form a first concentration, the accumulated sample component being carried into the first portion by the carrier fluid stream;
  g. manipulating the temperature of the first portion to release the first concentration into the carrier fluid stream in the form of a first chemical pulse;
  h. causing the first chemical pulse to be carried in the direction of the carrier fluid stream flow toward the second portion;
  i. accumulating the first chemical pulse in said outlet portion so as to focus and hold the first chemical pulse therein for a period of time and form a second concentration which is more compact in distance than the first chemical pulse, sample components of the first chemical pulse being carried to the outlet portion by the carrier fluid stream;
  j. manipulating the temperature of the first portion to accumulate at least one second sample component therein for a period of time, the at least one second sample component being carried into the first portion by the carrier fluid stream;
  k. manipulating the temperature of the second portion so as to release the second concentration into the carrier fluid stream in the form of an outlet chemical pulse, the outlet chemical pulse being of shorter duration than the first chemical pulse;
  l. manipulating the temperature of the second portion such that a subsequent chemical pulse is retained therein; and
    wherein travel of a first concentration from the first portion to the second portion in step (h) is delayed such that:
    steps (d), (e), (j) and (l) may occur simultaneously during an interval of time; and
    steps (g) and (k) may occur simultaneously during an interval of time.

The present invention provides method "A," wherein the modulator tube includes a portion that is shaped in the form of a loop.

The present invention provides method "A," wherein steps (d), (e), (j), (l), (g), and (k) are effected within a single thermal manipulation zone.

The present invention provides method "A," wherein a first portion and a second portion are formed by passing said tube more than once through said single thermal manipulation zone, such that a delay loop between said first portion and said second portion is formed.

The present invention provides method "A," wherein said thermal manipulation zone comprises a stream of cooled gas.

The present invention provides method "A," wherein said stream of cooled gas is pulsed.

The present invention provides method "A," wherein said thermal manipulation zone comprises a stream of heated gas.

The present invention provides method "A," wherein said stream of heated gas deflects a stream of cooled gas.

The present invention provides method "A," further comprising the steps of:
  m. measuring the time of travel of a concentration of a sample substance through said delay loop;
  n. measuring the length of said delay loop; and
  o. calculating the velocity of said concentration of sample substance through said delay loop.

The present invention provides method "A," further comprising determining a van't Hoff plot for a sample substance.

The present invention provides method "A," wherein said modulator tube is part of a one-dimensional gas chromatograph.

A thermal modulation apparatus is provided, referred to herein as apparatus "B," for generating chemical pulses in a fluid stream flowing through a modulator tube, said apparatus comprising:
  a modulator tube having an inlet, a first portion which is a length of said tube in communication with said inlet, a second portion which is a length of said tube in communication with said first portion, and an outlet portion in communication with said second portion;
  a means for creating a fluid stream in a direction through said modulator tube to produce a carrier fluid stream;
  a means for introducing a sample comprising one or more sample components into the carrier fluid stream;
  a means for manipulating the temperature of the first portion to cause at least a portion of the sample to be retained therein;
  a means for manipulating the temperature of the second portion such that the one or more components will be retained therein;
  a means for accumulating a sample component in the first portion for a period of time to form a first concentration of sample, the accumulated sample substance being carried into the first portion by the carrier fluid stream;
  a means for manipulating the temperature of the first portion to release the first concentration into the carrier fluid stream in the form of a first chemical pulse;
  a means for causing the first chemical pulse to be carried in the direction of carrier fluid stream flow toward the second portion;
  a means for accumulating the first chemical pulse in said outlet portion so as to focus and hold the first chemical pulse therein for a period of time and form a second concentration of sample which is more compact in distance than the first chemical pulse, sample substances of the first chemical pulse being carried to the outlet portion by the carrier fluid stream;
  a means for manipulating the temperature of the first portion to accumulate more sample substance therein for a period of time, the sample substance being carried into the first portion by the carrier fluid stream;

a means for manipulating the temperature of the second portion so as to release the second concentration into the carrier flow stream in the form of an outlet chemical pulse, the outlet chemical pulse being of shorter duration than the first chemical pulse;

a means for manipulating the temperature of the second portion such that a subsequent chemical pulse is retained therein; and a means for delaying the travel of the first chemical pulse to the second portion, such that the temperatures of the first and second portions can be manipulated simultaneously.

Apparatus "B" is provided wherein said means for manipulating the temperature of the first portion to release the first concentration into the carrier fluid stream comprises a retention alteration means.

Apparatus "B" is provided wherein said means for manipulating the temperature of the first portion to release the first concentration into the carrier fluid stream comprises a stream of heated gas directed onto the first portion.

Apparatus "B" is provided wherein said means for manipulating the temperature of the second portion to release the second concentration into the carrier fluid stream comprises a retention alteration means.

Apparatus "B" is provided wherein said means for manipulating the temperature of the second portion to release the second concentration into the carrier fluid stream comprises a stream of heated gas directed onto the second portion.

Apparatus "B" is provided, said apparatus further comprising means for measuring the velocity of a chemical pulse between the first portion and the second portion.

Apparatus "B" is provided, said apparatus further comprising means for constructing a van't Hoff plot.

Apparatus "B" is provided, said apparatus further comprising means for predicting the velocity of a chemical substance in a tube.

Apparatus "B" is provided for increasing the sensitivity of a one-dimensional gas chromatograph.

Apparatus "B" is provided wherein means for manipulating the temperature of a first portion and a second portion comprise a single pulsed stream of gas.

A thermal modulation apparatus, referred to herein as apparatus "C," is also provided for generating chemical pulses in a fluid stream flowing through a modulator tube, said apparatus comprising:

a modulator tube having an inlet, a first portion in communication with said inlet at a first portion inlet port, a second portion in communication with said first portion at a second portion inlet, and an outlet portion in communication with said second portion, wherein at least a portion of the modulator tube is formed in a loop such that the first portion inlet port and the second portion inlet are adjacent one another such that they can be thermally modulated simultaneously with a single thermal modulating device;

an inlet port for introducing a sample comprising one or more sample components into a carrier fluid stream flowing through the modulator tube; and at least one thermal modulating device adapted to direct at least one stream of heated gas, cooled gas, or both heated gas and cooled gas, toward said first and second inlet portions simultaneously.

The apparatus "C" is provided, further comprising a carrier fluid stream flowing through the modulator tube.

Another thermal modulation apparatus is provided according to the invention for generating chemical pulses in a fluid stream flowing through a modulator tube, said apparatus comprising:

a modulator tube having an inlet, a first portion in communication with said inlet, a second portion in communication with said first portion, and an outlet portion in communication with said second portion;

a fluid stream in a direction through said modulator tube to produce a carrier fluid stream;

an injection port for introducing a sample comprising one or more sample components into the carrier fluid stream; and a thermal modulator that is adapted to:

manipulate the temperature of the first portion to cause at least a portion of the sample to be retained therein;

manipulate the temperature of the second portion such that sample will be retained therein;

accumulate a sample component in the first portion for a period of time to form a first concentration of sample, the accumulated sample component being carried into the first portion by the carrier fluid stream;

manipulate the temperature of the first portion to release the first concentration into the carrier fluid stream in the form of a first chemical pulse;

cause the first chemical pulse to be carried in the direction of carrier fluid stream flow toward the second portion;

accumulate the first chemical pulse in said outlet portion so as to focus and hold the first chemical pulse therein for a period of time and form a second concentration of sample which is more compact in distance than the first chemical pulse, sample components of the first chemical pulse being carried to the outlet portion by the carrier fluid stream;

manipulate the temperature of the first portion to accumulate a second sample component therein for a period of time, the second sample component being carried into the first portion by the carrier fluid stream as an additional chemical pulse;

manipulate the temperature of the second portion so as to release the second concentration into the carrier flow stream in the form of an outlet chemical pulse, the outlet chemical pulse being of shorter duration than the first chemical pulse;

manipulate the temperature of the second portion such that a subsequent chemical pulse is retained therein; and delay the travel of the first chemical pulse to the second portion, such that the temperatures of the first and second portions containing the additional chemical pulse and the second chemical pulse, respectively, can be manipulated simultaneously.

FIGS. 1a and 1b show a schematic of the loop modulator in side and end views, respectively. A length of tubing, the modulator tube 1, sustains a flow of carrier gas, and is coiled so as to pass twice through the path of a jet tube 2 conducting cold gas to a first portion of the modulator tube 3, and simultaneously to a second portion of the modulator tube 4, thereby forming the first and second stages, respectively, of a two-stage thermal modulator. Disposed at right angles to the cold jet is a hot jet tube 5 sustaining a flow of gas pulsed by means of an electronically controlled solenoid valve 6. The hot jet gas stream is heated by a heater block 7 carrying a cartridge heater 8. In the front view of the apparatus, the cold jet tube 2 partially eclipses the hot jet tube 5, and totally eclipses the cartridge heater 8. The front view makes it clear that the first modulator stage, i.e., the first modulator tube portion 3, is upstream, with respect to carrier gas flow direction, of the second modulator stage, or second modulator tube portion 4.

Figure 2:
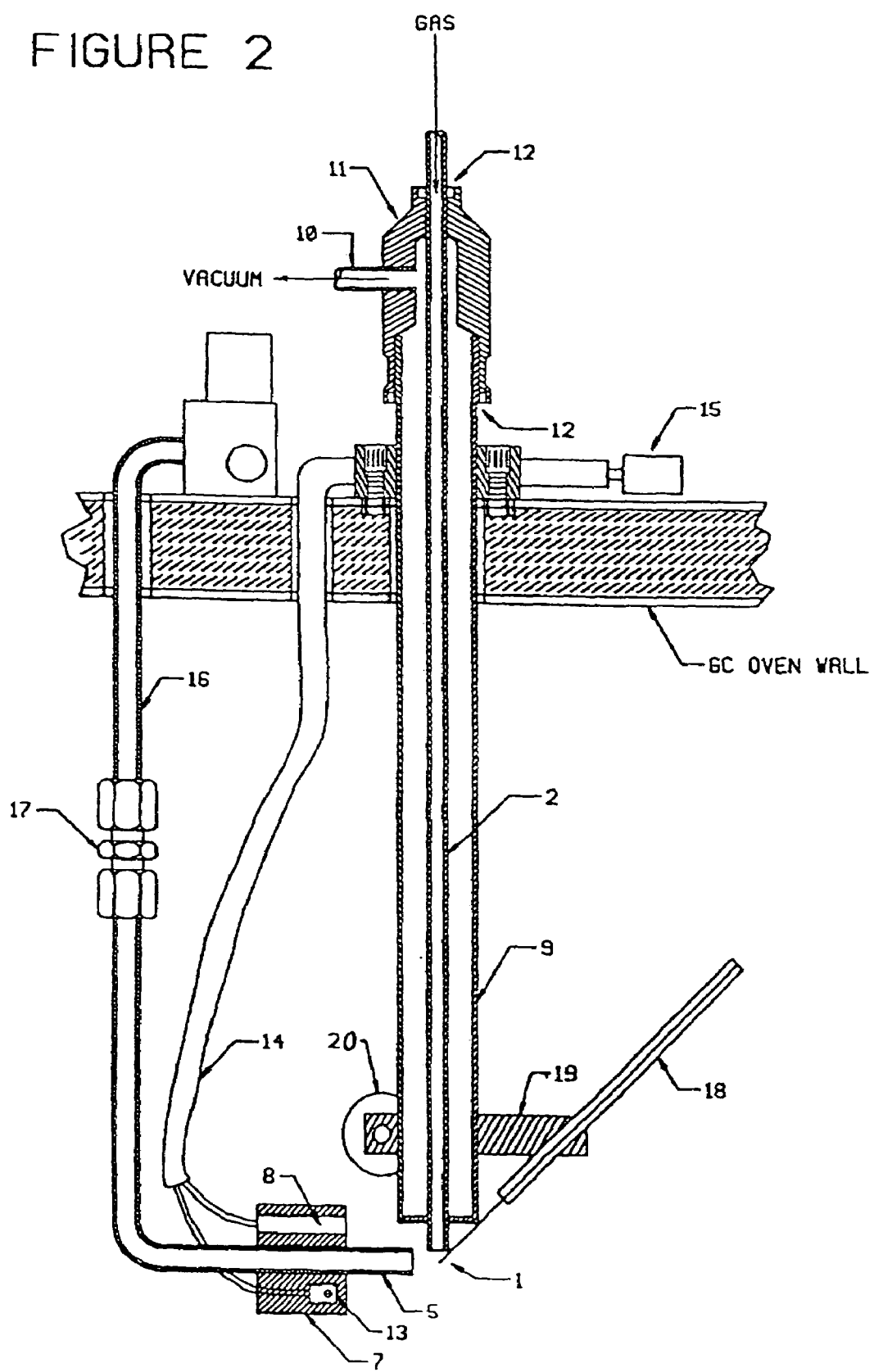

FIG. 2 depicts the mechanical structure of the loop modulator in more detail. The cold jet tube 2 is enveloped in a vacuum jacket 9 evacuated at a port 10 mounted in a machined bulkhead 11. The bulkhead 11, cold jet tube 2, and vacuum envelope 9 are secured together by silver soldered joints at 12. Disposed at right angles to the cold jet is the hot jet tube 5, heated by heater block 7 and cartridge heater 8. An RTD temperature sensor 13, connected via cable 14, and electrical connector 15 to a temperature control circuit (not shown), provides temperature regulation of the heater block. The hot jet tube 5 is fastened to a gas supply tube 16 by means of a Swagelock union 17. The gas supply tube connects to a pulsed solenoid valve (not shown). The valve solenoid is actuated by the application of 24 Volt DC, controlled by a solid-state relay, as is commonly known in electronic art. The valve is pulsed by means of a pulse generator board (Model 6602, National Instruments, Austin, Tex.), controlled by a software interface written in C++, according to instructions supplied by the manufacturer of the pulse board.

The modulator tube 1 is housed in a column holder 18, which is inserted into a slotted clamp 19, operated by a thumbscrew 20. The column holder engages the column clamp by friction, so that its position in the slotted clamp is easily adjustable. The vertical position of the clamp 20 may be adjusted up and down, whereby the modulator stages may be positioned in the path of the hot jet, or below the path of the hot jet. In either vertical position, the modulator stages remain in the path of the cold jet gas.

FIGS. 3a and 3b depict the column holder 18 as a rectangular sheet of stainless steel with the edges folded on a bending brake, thereby forming a pair of "wings" 119 that hold the column 1 in place. The "wings" 119 are sprung so that they create friction drag when the column holder 18 is inserted into the slotted clamp (not shown). Insertion of the column into the holder is a simple process. The modulator column is wound into a coil 20, which acts as a delay line, or delay loop, and is inserted into the folded metal wings 19, whereby the coil is captured in the column holder. A first modulator stage 3 is constructed by pushing the carrier input leader 21 toward the column holder 18, thereby extending a column winding toward the end of the column holder opposite that of the carrier input leader. The second modulator stage 4 is constructed in like manner by pushing the carrier output leader. Once positioned in the column holder 18, the modulator tube is tacked with polyimide glue to prevent the coils and modulator stages from moving during subsequent handling. As shown in FIG. 3b, the column coil 20 and modulator stages 3 and 4 spring toward the inner walls of the bent-over wings, such that the column suspends itself in the mid-plane of the column holder.

If the hot jet is pulsed for a period of time shorter than the time required for the chemical pulse to travel around the delay loop 20, such that the cold spot on the downstream modulator stage 4 is re-established prior to the arrival of the chemical pulse, then the chemical pulse is accumulated in the downstream modulator stage 4, thereby effecting two-stage thermal modulation.

Figure 4A:
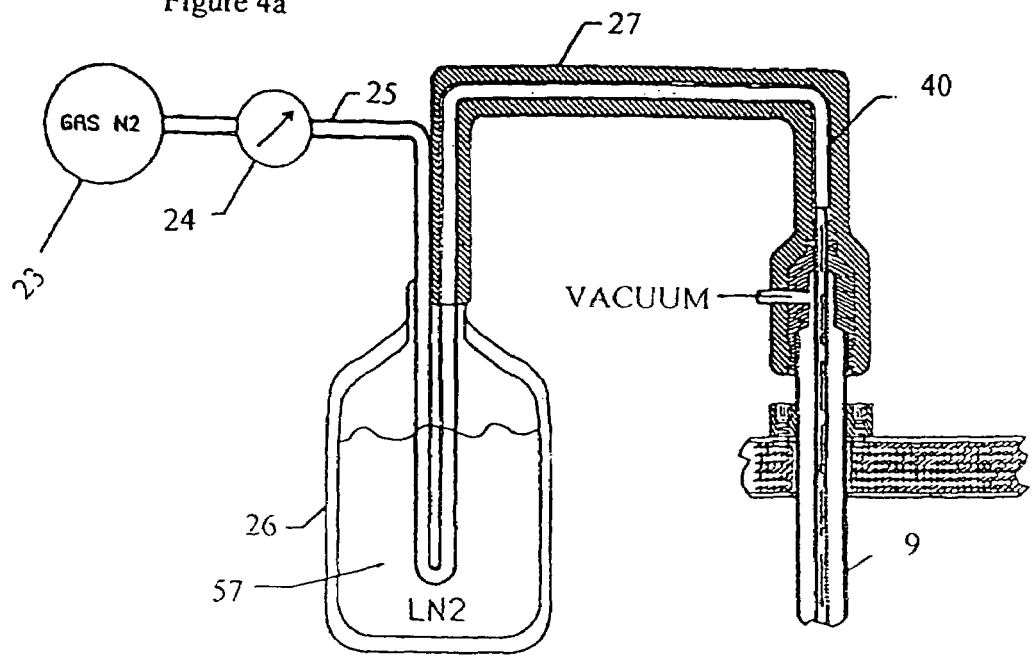
FIG. 4a is a cross-sectional side view of an embodiment of the present invention showing a heat exchanger.
Figure 4B:
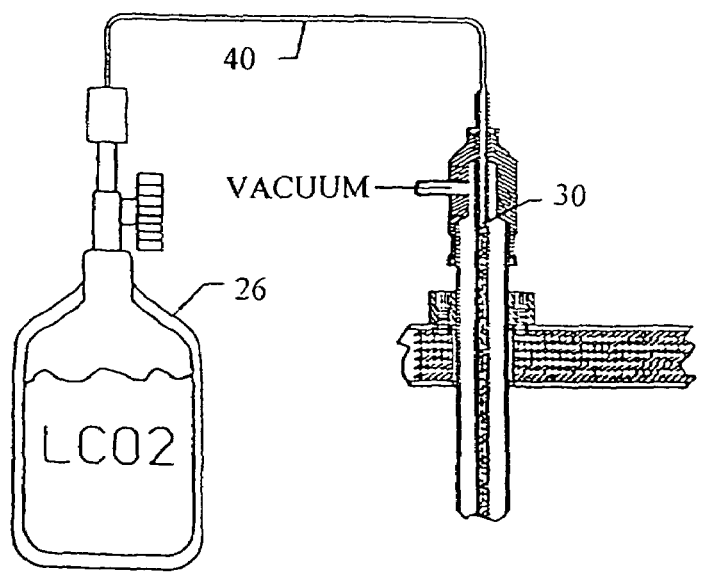
FIG. 4b is a cross-sectional side view of an embodiment of the present invention showing a source of the cold gas jet.

Many methods exist for cooling the gas delivered to the cold jet. In FIGS. 4a and 4b, a method for producing a gas jet with a temperature of $-110°$ C. to $-189°$ C. is indicated. A source of gaseous nitrogen 23 directed through a pressure regulator 24 supplies a stream of gas to a tube 25, which conveys the gas to a heat exchange coil 26 bathed in a liquid nitrogen bath 57. The latter is contained in a standard laboratory dewar 28. The stream of nitrogen gas cools to near liquid nitrogen temperature in the heat exchange tube, and passes to the cold jet tube (not shown) via connecting tube 40, which is surrounded by an insulation sheath 27. The sheath 27 may be made of plastic foam sleeving of the type commonly used to insulate household plumbing pipes, in which case, gas temperatures within the cold jet tube reach temperatures of $-110°$ C. to $-170°$ C., depending on the gas flow rate and the amount of time the apparatus is allowed to cool. The insulation sheath 27 can also be a vacuum jacketed transfer line of the type commonly employed in cryogenic art. In that case, jet gas temperature of $-189°$ C. is readily achieved. At this temperature, methane gas can be thermally modulated.

FIG. 4b depicts cooling the jet with gaseous carbon dioxide withdrawn from the headspace of a valved liquid $CO_2$ cylinder 28. The $CO_2$ is conveyed through a steel (0.063 inch o.d., 0.030 inch i.d.) transfer tube 29 at high pressure (c.a. 1,000 psi). The end of this transfer tube 29 is crushed to restrict the flow rate of $CO_2$ gas exiting the tube to approximately 10 standard liters per second. The work of expansion cools the $CO_2$ gas to about $-77°$ C., suitable for thermal modulation across the C9+ carbon range.

It is also possible to direct-liquid $CO_2$ to a crushed tube restrictor, in which case the heat of vaporization must be supplied to the expanding liquid jet, in order to prevent the formation of dry ice in the cold jet tube. One method of supplying the heat of vaporization is to admix the $CO_2$ with a stream of nitrogen "makeup" gas admitted to the cold jet tube via a "tee" fitting, and controlled by means of a needle valve. It is found that the temperature of the $CO2/N_2$ mixture exiting the jet tube can be smoothly controlled by adjusting the needle valve over a temperature range from $-85°$ C. to $-40°$ C. At temperatures of $-80°$ C. or below, microscopic dry ice particles form in the jet of gas exiting the cold jet tube. These particles scatter light, and permit the shape of the gas jet to be seen by the operator.

Figure 5A:
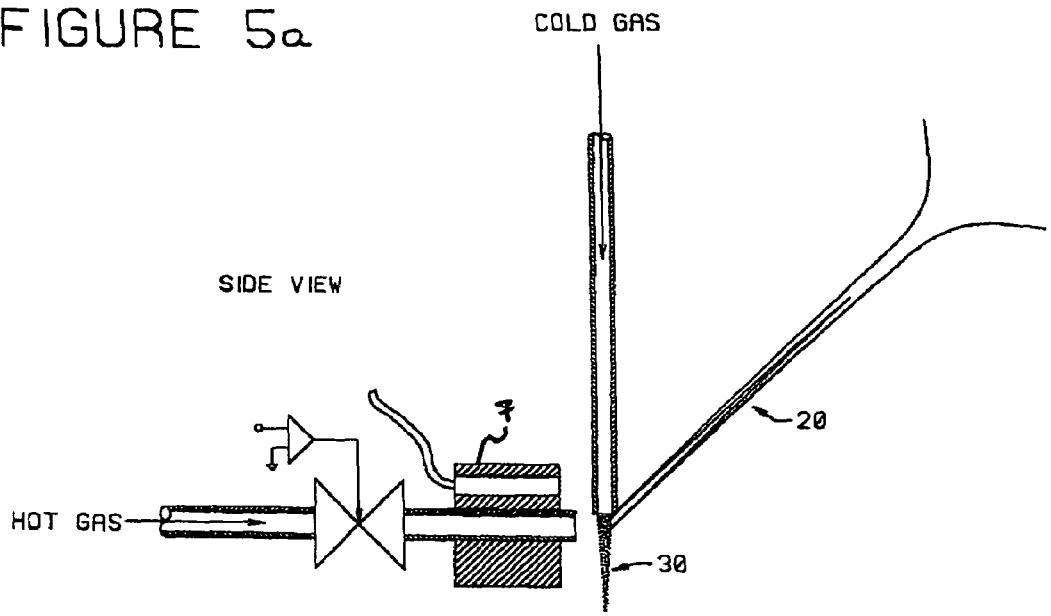
FIG. 5a is a side view in partial phantom of an embodiment of the present invention depicting the gas flow of the cold gas jet.

FIG. 5 illustrates the use of a liquid $CO_2/N_2$ jet, the temperature of which was adjusted by means of a variable Nitrogen makeup flow to a value at which dry ice formation made the cold jet visible. The cold jet was found to be laminar, and exhibited the characteristic cone shape 30 of a moving laminar column of gas equilibrating with a surrounding gas at a different temperature (candle effect). The portions of the modulator tube 20 immersed within this cold jet accumulated chemical substances, i.e., functioned as thermal modulator stages in accumulation mode.

Figure 5B:
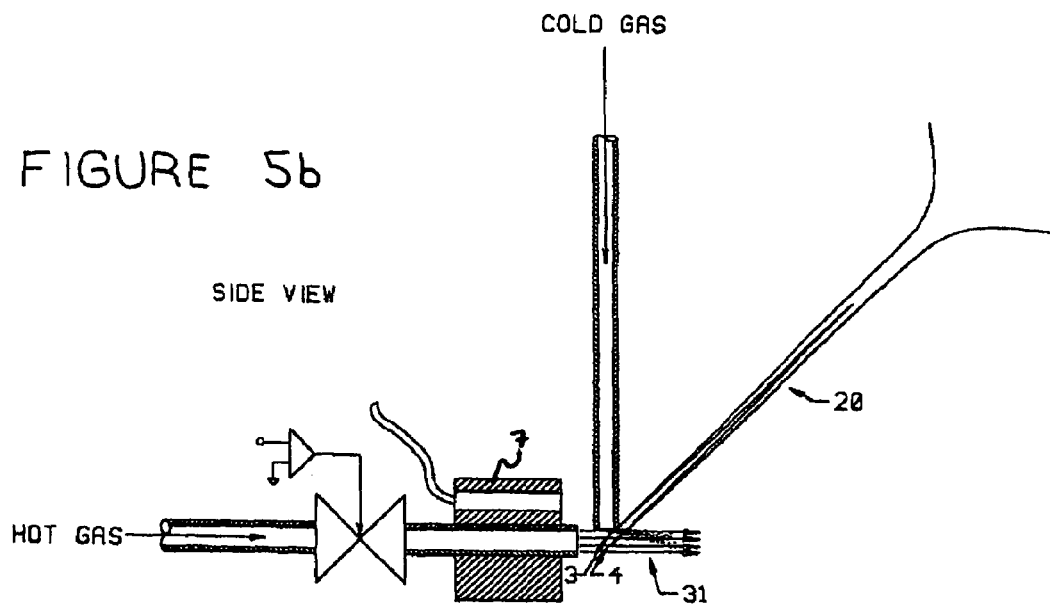
FIG. 5b is a side view in partial phantom of an embodiment of the present invention showing the interaction of the cold gas jet and the hot gas jet.

FIG. 5b depicts the loop modulator in release mode. A "hot" jet 31 comprised of room temperature gas (no power applied to the heater block) preserved dry ice particles in the jet, which permitted the operator to observe that the cold jet was deflected away from the modulator stages 3 and 4. When the hot jet heater block 7 was powered, such that the heater block temperature was maintained at about 100° C. or higher, the dry ice particles in the cold jet disappeared the moment the jot jet fired.

Under thermal modulation conditions, if the operator places a finger below the modulator tube, he or she can feel the cold jet disappear when the hot jet pulses—a simple demonstration of the jet deflection mode. This deflection mode is possible because low-flow cold jets are easily diverted by high-flow hot jets. Deflection mode eliminates the need to pulse the cold jets, as has been practiced in prior art jet modulators. The resulting simplification of apparatus is attributable to the discovery that a low-flow cold jet can effectively cool a thermal modulator stage even when exposed to turbulent air in a stirred oven bath. (Prior art jet designs of Ledford et al had used low-flow cold jets that were shielded from the stirred oven bath by the column holder assembly).

It is useful to present sample substances, such as n-alkanes, to a thermal modulator continuously, so as to monitor modulation pulses continuously while modulation parameters are varied. A simple way to present sample continuously is to load a common 10 µl syringe with a liquid hydrocarbon, such as decane, insert the syringe needle into the GC injector, and leave it there. After an initial surge of sample matter, an exponential decay of the sample concentration is observed, which settles into a long tail of nearly constant amplitude, as sample material diffuses from the syringe into the GC injector. In this way, a steady stream of sample substance can be continuously presented to a thermal modulator for many tens of minutes.

If, in the presence of continuously presented sample, the hot jet is pulsed on for a period of time longer than the time required for a chemical pulse to traverse the delay loop, the accumulated contents of both modulator stages will be released. If the modulator tube is connected to a GC detector, such as an FID, both released pulses can be observed, as is apparent from FIG. 6.

Figure 6:
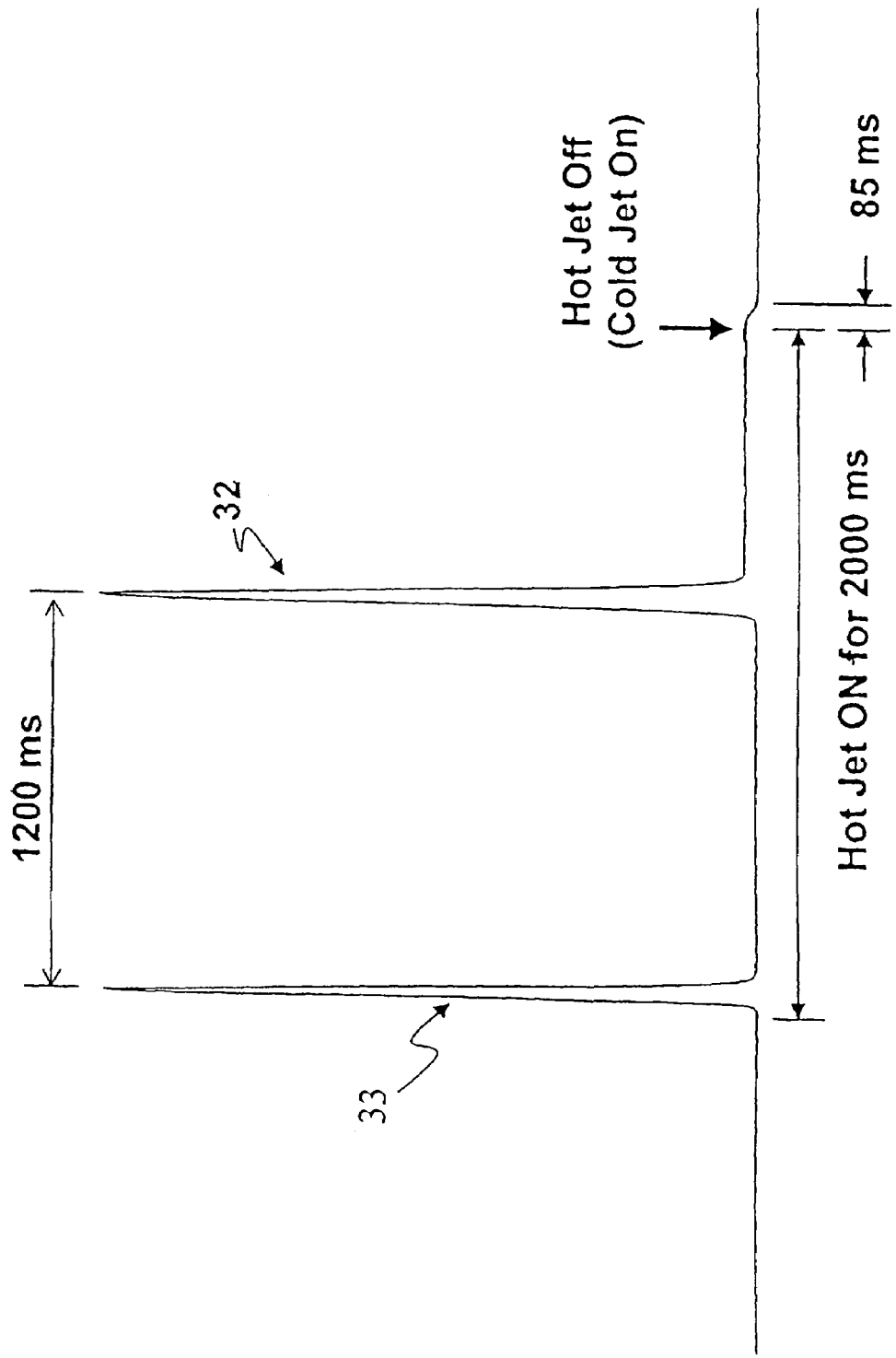
FIG. 6 is a graphical representation of the peak height and spacing of a sample that has been processed by an embodiment of the present invention.

In FIG. 6, the left-hand pulse 33 is the chemical pulse released from the second stage of the thermal modulator by the hot jet. It contains only the amount of material present in the delay loop at the moment the cold spots in the modulator stages were established during the previous sample accumulation step (the delay loop "clears" into the second modulator stage shortly after the cold jet is turned on.) The right-hand pulse 32 is the chemical pulse released from the first stage of the thermal modulator by the hot jet. It contains the amount of material continuously accumulated throughout an entire thermal modulation cycle in the presence of a continuous sample stream, as described above.

The time difference $\Delta t$ between the maxima of the two chemical pulses released from the two modulator stages is the time required for the chemical pulse formed by the first modulator stage to travel around the delay loop.

If the length, L, of the delay loop is known, then the ratio $L/\Delta t$ is the average velocity, $|u|$, of the first chemical pulse in the delay loop. Because the length of the delay loop can be made very small compared to the overall length of a capillary column, the average velocity $|u|$ closely approximates the instantaneous velocity $u(x)$ at the midpoint, x, of the delay loop. The velocities of both retained and unretained substances within the body of the modulator tube can be measured in this way.

The velocity of an unretained chemical substance is that of the carrier gas, $u_0$. If both u for a chemical substance and $u_0$ for a carrier gas are measured in the manner described above, then the well known relation $k=u/u_0-1$ yields the partition coefficient k for a substance retained by the modulator tube. Determination of k, together with a knowledge of the column phase ratio $\beta$, permit calculation of the free energy of solution, $\Delta G$, of a given analyte on a given stationary phase coating on the inner wall of a modulator tube. Knowledge of the $\Delta G$ for a given analyte on a given stationary phase permits the chromatographic behavior of that analyte to be predicted on any capillary column coated with that stationary phase. Numerical prediction of gas chromatograms is then possible, as is numeric optimization of chromatographic conditions for such thermodynamically characterized analytes.

The ease with which the present invention permits in-situ velocity measurements within a capillary tube permits many quantitative investigations of physical and physico-chemical processes in capillary columns that were not possible with prior gas chromatographic art. For example, measuring velocity at different positions along a capillary column would permit an experimental velocity profile to be determined. Such a profile would facilitate quantitative tests of gas compression theory in capillary columns, gas chromatographic measurement of thermodynamic properties of analytes, quantitative and experimentally verifiable treatments of chemical pulse formation in thermal modulators, and tuning of secondary columns in GC×GC.

It is a surprising aspect of the present invention that in-situ measurement of the velocity of a chemical vapor within the body of a capillary tube is so easily performed. In this, and other respects, the present invention is a novel scientific instrument.

Typical Operating Conditions and Results

Liquid Nitrogen Cooled Jets. Liquid nitrogen cooled jets produce modulation pulses of some 30 to 36 milliseconds duration (base of peak). Peaks as narrow as 24 milliseconds have been observed, narrower than any observed with prior art jet modulators.

Typical operating conditions for a liquid nitrogen cooled loop modulator would be:

| | |
|---|---|
| Inlet Temperature: | 250° C. |
| Inlet Pressure: | 20 psi |
| Split Ratio: | 300 |
| Carrier Gas: | Hydrogen |
| Modulation Period: | 3 seconds |
| Hot Jet Duration: | 200 ms |
| Modulator Tube i.d. | 0.1 mm |
| Modulator Tube o.d. | 0.2 mm |
| Modulator Stationary Phase | None (bare deactivated FSOT) |
| Cold Jet Temperature: | −130° C. |
| Cold Jet Flow Rate: | 5 standard liters per second |
| Oven Temperature | +35° C. |
| Hot Jet Temperature | +100° C. |
| Delay Loop Length: | 60 cm |
| Detector: | FID |
| Digitizing Frequency: | 200 Hz |

Under these conditions, chemical pulses formed by thermal modulation of propane are 30 milliseconds wide at base. Organic substances in the C3+ range modulate readily under the same conditions. Hexadecane exhibits modulation pulse widths of 48 ms at base. Modulation peaks are symmetric. Holdup time in the modulator is greater than ten seconds.

Carbon Dioxide Cooled Jets. Carbon dioxide cooled jets are suitable for modulating organic substances in the C9+ range if $CO_2$ gas is employed as the cold jet refrigerant, and over the C8+ range is $CO_2$ liquid is employed as the cold jet refrigerant, on uncoated modulator tubes. The use of nitrogen makeup gas in the case of $CO_2$ liquid refrigerant prevents dry ice buildup in the cold jet tube, because the makeup gas supplies heat of vaporization to the expanding $CO_2$ jet.

Typical conditions for gaseous $CO_2$ modulation are:

| | |
|---|---|
| Inlet Temperature: | 250° C. |
| Inlet Pressure: | 20 psi |
| Split Ratio: | 300 |
| Carrier Gas: | Hydrogen |
| Modulation Period: | 3 seconds |
| Modulator Tube i.d. | 0.1 mm |
| Modulator Tube o.d. | 0.2 mm |
| Modulator Stationary Phase | None (bare deactivated FSOT) |
| Cold Jet Temperature: | −77° C. |
| Cold Jet Flow Rate: | 10 standard liters per second |
| Oven Temperature | +120° C. |
| Hot Jet Temperature | +220° C. |
| Hot Jet Duration: | 100 ms |
| Delay Loop Length: | 60 cm |
| Detector: | FID |
| Digitizing Frequency: | 200 Hz |

Under these conditions, decane exhibits symmetrical modulation pulses 36 milliseconds wide at base.

Hot Jet vs. Ambient Oven Heating. By moving the column holder clamp up or down on the vacuum jacket of the cold jet, it is possible to position the modulator stages in or out of the path of the hot jet. In the latter case, the modulator stages are heated by the stirred air bath in the GC oven. This experiment permits comparison of the two heating modes, hot jet vs. ambient oven, under identical modulation conditions. Under the conditions described above, for both liquid nitrogen and $CO_2$ cooled loop modulators, ambient oven heating of modulator stages produced asymmetric, tailed peaks, 70 to 75 milliseconds wide at base for dodecane. Hot jet heating of modulator stages produced symmetric peaks 30 to 36 milliseconds wide at base for dodecane. The asymmetry of the oven-heated peak consists of an exponential tail on the rising edge of the peak, which indicates sluggish release from the second stage of the thermal modulator. It should be noted that the release profile is functionally related to the acceleration of a chemical pulse.

In-Situ Velocity Measurement. If the duration of the hot jet pulse is extended to a value greater than the travel time of a chemical substance around the delay loop, chemical pulses from both modulator stages are released from the loop. This permits velocity measurement, as described above, if the length of the delay loop is known. The velocity measurement can be conducted with or without stationary phase in the modulator tube.

The velocity measurements can be made in the presence of a full GC×GC column set. In this case, some broadening of modulation pulses is expected as a result of partitioning on the stationary phase of the secondary column. However, the secondary column can have no effect on the time difference between chemical pulses emitted from the first and second modulator tube stages. Because both pulses are composed of the same chemical substance, both must have identical velocities on the secondary column, under isothermal conditions, which preserves the time difference between the chemical pulses, even though they traverse the stationary phase of a secondary column.

Typical conditions for a velocity measurement with a GC×GC column set installed in the gas chromatograph are:

| | |
|---|---|
| Inlet Temperature: | 250° C. |
| Inlet Pressure: | 20 psi |

-continued

| | |
|---|---|
| Split Ratio: | 300 |
| Carrier Gas: | Hydrogen |
| Sample: | Butane, Continuous |
| Modulation Period: | 4 seconds |
| Modulator Tube i.d. | 0.1 mm |
| Modulator Tube o.d. | 0.2 mm |
| Modulator Stationary Phase | None (bare deactivated FSOT) |
| Cold Jet Temperature: | −77° C. |
| Cold Jet Flow Rate: | 27 standard liters per second |
| Oven Temperature | +150° C. |
| Hot Jet Temperature | +250° C. |
| Hot Jet Duration: | 2000 ms |
| Delay Loop Length: | 65 cm |
| Detector: | FID |
| Digitizing Frequency: | 200 Hz |
| Primary Column: | 10 meter long |
| | 0.1 mm i.d. |
| | Methylsilicone, 0.25μ film thickness |
| Secondary Column: | 0.5 meter long |
| | 0.1 mm i.d. |
| | Carbowax, 0.1μ film thickness |

Under these conditions, the modulation profile shown in FIG. 6 was obtained, which exhibits features that cannot be observed with any prior art thermal modulation system.

In FIG. 6, a butane peak 32 released from the second stage of the thermal modulator is visible and distinguishable from a butane peak 33 released from the first stage of the thermal modulator. The separation between the two butane peaks is 1200 ms. Because the modulator tube was 0.65 meter long, the average velocity of the butane through the delay loop was 0.65 meter/1.2 second=0.54 meter/second.

Referring to FIG. 6, the chemical pulse 33 from the second stage of the thermal modulator has a more complex shape than the chemical pulse 32 from the first stage. An initial surge in the peak intensity of the first stage chemical pulse is followed by a plateau, or "shelf" 34 lasting 800 ms. This plateau is attributable to sample material gated to the modulator by a hot jet pulsed on for 2000 msec. Note that the sum of the loop delay period and the duration of the plateau equals the hot jet duration (see parameters above). Clearly, the plateau is caused by the fact that sample from the injector was continuously presented to the column (by leaving a loaded syringe in the GC injector). Once the first stage chemical pulse traverses the second stage of the modulator, the continuous sample stream will "chase" it, thereby forming a plateau on the trailing edge of the first stage modulation pulse.

The plateau 34 falls to baseline sharply at 35, when the hot jet is turned off. At that moment, the cold jet once again falls onto the modulator stages, which begin accumulating chemical substances. Consequently, butane is removed from the carrier gas flow. The detector registers removal of butane from the carrier flow as a decrease in the butane signal intensity, observed at 35 in FIG. 6. The butane signal intensity reached baseline in about 85 milliseconds, indicating the length of time required to cool the first modulator stage to a temperature at which butane is fully retained (by this particular modulator tube, which was uncoated) Clearly, the accumulation (cooling) profile observed at the edge of the plateau signal would permit detailed study of cooling and retention processes within a capillary tube.

Certain details of the modulation process apparent in FIG. 6 would not be observable with any prior art thermal modulator. In all prior art designs, the spatial separation of the modulator stages was too small to permit temporal separation of the first stage chemical pulse from the second stage chemical pulse. With first and second chemical pulses merged in prior art devices, details of the thermal modulation process were obscured. In particular, neither the terminal velocity nor the release profile (a function of acceleration) of chemical pulses within prior art thermal modulators could be directly determined, whereas the present invention facilitates such measurements.

Clearly, many variations of the present invention are possible within the scope of the above description. For example, multiple delay loops can be passed through a jet structure, such as to produce dual column, dual detector chromatography. More than one jet structure can be employed on a gas chromatograph. A cold jet can be pulsed by a valve instead of operated continuously. A chemical pulse width can be measured by varying the duration of the hot jet systematically, and monitoring the growth of the first stage chemical pulse signal as a function of hot jet duration. Closed cycle refrigerators, rather than open cycle refrigeration techniques, can be used with the loop modulator to eliminate consumption of cryogens. Many other variations can be envisioned within the scope of the present invention.

Although the present invention has been described in connection with preferred embodiments, it will be appreciated by those of skill in the art that additions, modifications, substitutions, and deletions not specifically described may be made without departing from the spirit and scope of the invention defined in the appended claims.

What is claimed is:

1. A method of thermal modulation for generating chemical pulses in a fluid stream flowing through a modulator tube, said method comprising the steps of:
   a. providing a modulator tube comprising an inlet, a first portion in communication with said inlet, a second portion in communication with said first portion, and an outlet portion in communication with said second portion;
   b. creating a fluid stream in a direction through the modulator tube to produce a carrier fluid stream;
   c. introducing a sample into the carrier fluid stream, said sample comprising one or more chemical substances;
   d. manipulating the temperature of the first portion to cause at least a portion of the sample to be retained therein;
   e. manipulating the temperature of the second portion such that at least a portion of the sample will be retained therein;
   f. accumulating a sample component in the first portion for a period of time to form a first concentration, the accumulated sample component being carried into the first portion by the carrier fluid stream;
   g. manipulating the temperature of the first portion to release the first concentration into the carrier fluid stream in the form of a first chemical pulse;
   h. causing the first chemical pulse to be carried in the direction of the carrier fluid stream flow toward the second portion;
   i. accumulating the first chemical pulse in said outlet portion so as to focus and hold the first chemical pulse therein for a period of time and form a second concentration which is more compact in distance than the first chemical pulse, sample components of the first chemical pulse being carried to the outlet portion by the carrier fluid stream;
   j. manipulating the temperature of the first portion to accumulate at least one second sample component therein for a period of time, the at least one second sample component being carried into the first portion by the carrier fluid stream;
   k. manipulating the temperature of the second portion so as to release the second concentration into the carrier fluid stream in the form of an outlet chemical pulse, the outlet chemical pulse being of shorter duration than the first chemical pulse;
   l. manipulating the temperature of the second portion such that a subsequent chemical pulse is retained therein; and
   wherein travel of a first concentration from the first portion to the second portion in step (h) is delayed such that:
   steps (d), (e), (j) and (l) occur simultaneously during an interval of time; and
   steps (g) and (k) occur simultaneously during an interval of time.

2. The method of claim 1, wherein the modulator tube includes a portion that is shaped in the form of a loop.

3. A method according to claim 1, wherein steps (d), (e), (j), (l), (g), and (k) are effected within a single thermal manipulation zone.

4. A method according to claim 3, wherein a first portion and a second portion are formed by passing said tube more than once through said single thermal manipulation zone, such that a delay loop between said first portion and said second portion is formed.

5. A method according to claim 3, wherein said thermal manipulation zone comprises a stream of cooled gas.

6. A method according to claim 5, wherein said stream of cooled gas is pulsed.

7. A method according to claim 3, wherein said thermal manipulation zone comprises a stream of heated gas.

8. A method according to claim 7, wherein said stream of heated gas deflects a stream of cooled gas.

9. A method according to claim 4 further comprising the steps of:
   m. measuring the time of travel of a concentration of a sample substance through said delay loop;
   n. measuring the length of said delay loop; and
   o. calculating the velocity of said concentration of sample substance through said delay loop.

10. A method according to claim 9, further comprising determining a van't Hoff plot for a sample substance.

11. A method according to claim 1, wherein said modulator tube is part of a one-dimensional gas chromatograph.

12. A thermal modulation apparatus for generating chemical pulses in a fluid stream flowing through a modulator tube, said apparatus comprising:
   a modulator tube having an inlet, a first portion which is a length of said tube in communication with said inlet, a second portion which is a length of said tube in communication with said first portion, and an outlet portion in communication with said second portion;
   a means for creating a fluid stream in a direction through said modulator tube to produce a carrier fluid stream;
   a means for introducing a sample comprising one or more sample components into the carrier fluid stream;
   a means for manipulating the temperature of the first portion to cause at least a portion of the sample to be retained therein;
   a means for manipulating the temperature of the second portion such that the one or more components will be retained therein;
   a means for accumulating a sample component in the first portion for a period of time to form a first concentration of sample, the accumulated sample substance being carried into the first portion by the carrier fluid stream;

a means for manipulating the temperature of the first portion to release the first concentration into the carrier fluid stream in the form of a first chemical pulse;

a means for causing the first chemical pulse to be carried in the direction of carrier fluid stream flow toward the second portion;

a means for accumulating the first chemical pulse in said outlet portion so as to focus and hold the first chemical pulse therein for a period of time and form a second concentration of sample which is more compact in distance than the first chemical pulse, sample substances of the first chemical pulse being carried to the outlet portion by the carrier fluid stream;

a means for manipulating the temperature of the first portion to accumulate more sample substance therein for a period of time, the sample substance being carried into the first portion by the carrier fluid stream;

a means for manipulating the temperature of the second portion so as to release the second concentration into the carrier flow stream in the form of an outlet chemical pulse, the outlet chemical pulse being of shorter duration than the first chemical pulse;

a means for manipulating the temperature of the second portion such that a subsequent chemical pulse is retained therein; and a means for delaying the travel of the first chemical pulse to the second portion, such that the temperatures of the first and second portions can be manipulated simultaneously.

13. An apparatus according to claim 12, wherein said means for manipulating the temperature of the first portion to release the first concentration into the carrier fluid stream comprises a retention alteration means.

14. An apparatus according to claim 13, wherein said means for manipulating the temperature of the first portion to release the first concentration into the carrier fluid stream comprises a stream of heated gas directed onto the first portion.

15. The apparatus according to claim 12, wherein said means for manipulating the temperature of the second portion to release the second concentration into the carrier fluid stream comprises a retention alteration means.

16. The apparatus according to claim 15, wherein said means for manipulating the temperature of the second portion to release the second concentration into the carrier fluid stream comprises a stream of heated gas directed onto the second portion.

17. The apparatus according to claim 12, said apparatus further comprising means for measuring the velocity of a chemical pulse between the first portion and the second portion.

18. The apparatus according to claim 17, said apparatus further comprising means for constructing a van't Hoff plot.

19. The apparatus according to claim 18, said apparatus further comprising means for predicting the velocity of a chemical substance in a tube.

20. The apparatus according to claim 12, for increasing the sensitivity of a one-dimensional gas chromatograph.

21. The apparatus according to claim 12, wherein means for manipulating the temperature of a first portion and a second portion comprise a single pulsed stream of gas.

22. The method of claim 1, wherein at least a portion of the modulator tube is formed in a loop such that the first portion inlet and the second portion inlet are adjacent one another such that they are configured to be thermally modulated simultaneously with a single thermal modulating device and the manipulating the temperature of the first portion and the manipulating the temperature of the second portion comprise manipulating temperature with at least one thermal modulating device adapted to direct at least one stream of heated gas, cooled gas, or both heated gas and cooled gas, toward said first and second portions simultaneously.

23. A thermal modulation apparatus for generating chemical pulses in a fluid stream flowing through a modulator tube, said apparatus comprising:

a modulator tube having an inlet, a first portion in communication with said inlet, a second portion in communication with said first portion, and an outlet portion in communication with said second portion;

a fluid stream in a direction through said modulator tube to produce a carrier fluid stream;

an injection port for introducing a sample comprising one or more sample components into the carrier fluid stream; and a thermal modulator that is adapted to:

manipulate the temperature of the first portion to cause at least a portion of the sample to be retained therein;

manipulate the temperature of the second portion such that sample will be retained therein;

accumulate a sample component in the first portion for a period of time to form a first concentration of sample, the accumulated sample component being carried into the first portion by the carrier fluid stream;

manipulate the temperature of the first portion to release the first concentration into the carrier fluid stream in the form of a first chemical pulse;

cause the first chemical pulse to be carried in the direction of carrier fluid stream flow toward the second portion;

accumulate the first chemical pulse in said outlet portion so as to focus and hold the first chemical pulse therein for a period of time and form a second concentration of sample which is more compact in distance than the first chemical pulse, sample components of the first chemical pulse being carried to the outlet portion by the carrier fluid stream;

manipulate the temperature of the first portion to accumulate a second sample component therein for a period of time, the second sample component being carried into the first portion by the carrier fluid stream as an additional chemical pulse;

manipulate the temperature of the second portion so as to release the second concentration into the carrier flow stream in the form of an outlet chemical pulse, the outlet chemical pulse being of shorter duration than the first chemical pulse;

manipulate the temperature of the second portion such that a subsequent chemical pulse is retained therein; and delay the travel of the first chemical pulse to the second portion, such that the temperatures of the first and second portions containing the additional chemical pulse and the second chemical pulse, respectively, can be manipulated simultaneously.

* * * * *